US006568922B1

(12) United States Patent
Winsel

(10) Patent No.: US 6,568,922 B1
(45) Date of Patent: May 27, 2003

(54) PUMP CYLINDER AND METHOD OF COLLECTING PASTY MATERIALS, LIQUIDS, GASES AND/OR MOBILE OBJECTS

(76) Inventor: August Winsel, Fasanenstrasse 8a, 65779 Kelkheim (DE)

( * ) Notice: Subject to any disclaimer, the term of this patent is extended or adjusted under 35 U.S.C. 154(b) by 0 days.

(21) Appl. No.: 09/979,977

(22) Filed: Nov. 29, 2001

(30) Foreign Application Priority Data

Jun. 3, 1999 (DE) .......................... 199 25 481

(51) Int. Cl.[7] .............................. F04B 17/00
(52) U.S. Cl. .................. 417/379; 417/383; 417/392
(58) Field of Search ................. 417/379, 383, 417/392

(56) References Cited

U.S. PATENT DOCUMENTS

| | | | | |
|---|---|---|---|---|
| 3,739,573 A | * | 6/1973 | Giner ........................ | 60/671 |
| 3,994,789 A | * | 11/1976 | Langer et al. ............... | 205/579 |
| 4,369,235 A | * | 1/1983 | Bursell ...................... | 429/27 |
| 4,522,698 A | * | 6/1985 | Maget ....................... | 204/265 |
| 5,242,565 A | * | 9/1993 | Winsel ....................... | 204/265 |
| 5,382,331 A | * | 1/1995 | Banks ........................ | 205/781 |
| 5,538,605 A | * | 7/1996 | Joshi et al. .................. | 204/266 |

FOREIGN PATENT DOCUMENTS

EP  0 209 644  * 1/1987

* cited by examiner

*Primary Examiner*—Charles G. Freay
*Assistant Examiner*—Michael K. Gray
(74) *Attorney, Agent, or Firm*—Barnes & Thornburg

(57) ABSTRACT

A pump cylinder in which a pump plunger is guided which divides the cylinder into a forward and a rearward subspace, which, in the forward subspace, has a connection for taking in the fluid medium to be delivered, the rearward subspace of the pump cylinder containing one or several electrochemical gas consumption cells for a consumption gas, an electric circuit being provided which is constantly or temporarily connected with the electrodes of the gas consumption cell, is characterized in that the rearward part of the pump cylinder is filled with an electrochemical consumption gas, and the electric circuit is designed for causing a gas consumption current so that the pump cylinder forms a device for implementing a process for collecting pasty masses, liquids, gases and mobile objects for a previously determinable time period.

18 Claims, 4 Drawing Sheets

PUMP CYLINDER AND METHOD OF COLLECTING PASTY MATERIALS, LIQUIDS, GASES AND/OR MOBILE OBJECTS

BACKGROUND AND SUMMARY OF INVENTION

The invention relates to a pump cylinder a) in which a pump plunger is guided which divides the cylinder into a forward and a rearward subspace, b) which, in the forward subspace, has a connection for taking in the medium to be delivered, c) the rearward subspace of the pump cylinder having one or several electrochemical gas consumption cells for a consumption gas and d) an electric circuit being provided, which is constantly or temporarily connected with the electrodes of the gas consumption cell, as well as to a process.

In U.S. Patent Document U.S. Pat. No. 1,500,975, a machine is described which consists of three mutually connected cylinders and three plungers which are guided therein and are rigidly connected with one another. The three cylinders have different diameters. While the master cylinder is moved back and forth by a reciprocal admission of a vacuum and of atmospheric pressure to the spaces divided by the plunger, the two other cylinders and the plungers synchronously moved therein are used for the step-by-step compressing-on of air. In British Patent Document GB-PS 911,493, a lubricant dispenser is described. In the case of the latter, a lubricant pump presses the lubricant into a ring-shaped pipe which supplies one or several lubricating points. The ring-shaped pipe guides, by way of a pressure control valve, the excess lubricant back into the storage tank.

Systems are known and sold, by means of which pasty masses and liquids can be continuously delivered. In one of these systems (PERMA grease dispenser of the firm G. Satzinger in Bad Kissingen), a cylindrical body is divided into two subspaces by a membrane acting as a plunger. One subspace contains the medium to be delivered which is supplied by way of the spout mounted at one end. The second space contains a gas generating device which continuously generates hydrogen from a corrosion element. As a result, a pressure is built up, the plunger is displaced and the medium to be delivered is pressed out of the spout.

In that system, the corrosion element consists of a round zinc blank with a soldered-in molybdenum rod. When activated, it is charged into a caustic potash solution. Thereby the implementation of the gas generation is defined in a constant manner. It is a function of the temperature. The delivery speed itself is also a function of the counterpressure at the spout because, when the gas generating rate is constant, the volume production of the hydrogen is inversely proportional to the pressure.

With respect to a short-circuit element, the cell generating the hydrogen, as described in German Patent Document DE-PS 35 32 335 A1, offers the advantage that the generating of hydrogen can be precisely controlled by way of a resistor to be controlled from the outside. This cell consists of a variant consisting of a zinc anode and of a hydrogen cathode with caustic potash solution as an electrolyte and a separator which separates the anode and the cathode. In another variant of the cell, it generates oxygen as the propellant, in which case a reducible electrode, for example, of manganese dioxide $MnO_2$ or $AgO$ or another metal oxide, is used as the countercathode. An oxygen precipitation electrode is used as the anode. It is characteristic of the gas generating electrodes in both cases, for oxygen as well as for hydrogen, that the electrode material has an overpotential for the gas to be generated which is as low as possible, for which in both case Raney nickel and activated carbon can be used as a catalyst.

In German Patent Document DE 36 21 846 A1, a delivery system is described in the case of which the liquid to be delivered is transported by way of one or a plurality of pores in a body which is lyophobic with respect to the liquid to be delivered. This measure, which divides the delivery flow into a current of discrete drops, represents a pressure lock which makes the delivery flow less dependent on the counterpressure. This pressure lock may be arranged on the oncoming flow side and on the outgoing flow side between lyophilic porous bodies and may communicate with the latter.

Such delivery devices can be used in multiple manners. For example, the injection of insulin solution or other medications into the body by means of such delivery devices was suggested. An earlier invention (German Patent Document DE 3711714 C2 of Apr. 7, 1987) had the object of further developing a system of the initially mentioned type such that the delivery speeds can be predetermined and controlled and that the generating of the vacuum takes place by means of devices which are as simple as possible. The essence is a driving motor which consists of an essentially rigid driving cylinder with a driving plunger movable therein or a membrane acting as a plunger. In the starting condition, this driving cylinder is filled with an electrochemically effective gas, such as hydrogen or oxygen under atmospheric pressure. Inside this driving cylinder, a gas consumption cell is situated which has a gas consumption electrode and a suitable counterelectrode, which are arranged in a cell vessel. Between the electrodes, a separator is situated which has a suitable electrolyte. The contacts of the two electrodes are accessible outside the cylinder space or are to be operated from the outside.

When the closing takes place by way of an outside close-down circuit, a current flow is generated in the cell which per time unit consumes an equivalent quantity of the reaction gas and thereby generates a vacuum with respect to the outer atmosphere. This vacuum causes a movement of the driving plunger so that the latter can carry out an outside work operation.

In the case of the delivery system according to German Patent Document DE 3711714, the work operation consists of the movement of a pump plunger in a pump cylinder which preferably rigidly connected with the driving cylinder of the driving motor. The pump plunger is preferably also rigidly connected with the driving plunger of the driving motor. This pump cylinder contains the liquid to be delivered which, by means of the coupled movement of the two plungers is pressed out by way of the delivery spout or by way of a pressure lock.

Based on the existing state of the art, the invention uses a different approach which has not been recognized in that it designs and utilizes the pumping cylinders known per se for collecting many different types of samples. The invention achieves this by means of the following. Accordingly, the rearward part of the pump cylinder is filled with the gas which can be electrochemically consumed, and the electric circuit is designed for causing such a current that the gas is consumed, and the pump cylinder forms a device for collecting pasty masses, liquids, gases and mobile objects for a previously definable time period.

Although the present invention follows part of the teaching of German Patent Document DE 3711714 C2, in contrast to the latter, its object is not the distribution of fluid media but their collection. In many areas of manufacturing control, environmental production, medicine and biology, samples of pasty, liquid, gaseous substances or of mobile objects have to be collected, stored and tested, in which case the time periods for the collection of samples may be hours and months. This will be demonstrated by several examples:

Waste water from many large and small enterprises is led into the public sewage system. Proof of the introduction of toxic substances can be obtained only by a continuous sampling and the analysis of the samples.

The collecting of gas samples in the case of conversions in technical equipment also permits the clarification and the control of reaction sequences in gases.

The collecting of milk samples of automatically milked cows permits the determination of the average values of an animal's fat production. Samples of the body fluids of human beings and animals are also often helpful when diagnosing diseases.

The collecting of small animals and microbes in forests and fields and the collection of air samples in high-pollen seasons fall into the biological field.

In the food production field but also when monitoring the biology of bodies of water, the proof of germs or their exclusion by collecting samples is also of interest.

In a simple manner, the invention now provides a device for collecting pasty masses, liquids, gases and/or other mobile objects which permits the collecting of samples for a previously definable time period.

An advantageous constructive variant of the invention is characterized in that the consumption gas and the consumption cell in the driving cylinder are enclosed by a deformable plastic foil.

According to another preferred embodiment of the invention, the consumption gas contains oxygen and the consumption cell contains, in addition to a gas diffusion electrode for oxygen, an accumulator electrode as a counterelectrode, preferably in an alkaline electrolyte solution.

Particularly preferably, for ensuring the secure functioning of the device, a valve is present in the take-in pipe, which valve opens in the suction direction in the case of a vacuum and has a shut-off effect in the outflow direction in the case of excess pressure.

According to another particularly advantageous further development of the invention, the electric circuit is designed such that it permits a current flow in the consumption cell or cells only in the voltage window in which the gas consumption takes place and shuts off the current flow in the remaining voltage ranges. This ensures in an uncomplicated manner that the pump cylinder is operated only in the "collection and suction mode".

The electric circuit preferably contains an optical or acoustic signal generator which generates its signal when the current flow takes place in the voltage window which permits the gas consumption.

According to another advantageous variant of the invention, a starting resistor is present in addition to the adjustable working resistor, by way of which starting resistor the consumption cell will be short-circuited until the movement of the plunger starts. A manual switch or a pressure switch is also preferably provided for switching off the starting current and responds to the pressure difference at both sides of the plunger or to the movement of the plunger from the starting position of the plunger in the cylinder.

Generally, a consumption gas is used which is as pure as possible in order to utilize the full plunger stroke. However, by adding an inert contamination, the collecting operation can be limited because the inert gas remains in the plunger as residual gas.

Advantageously, time switches, photoresistors and/or photocells can be arranged as controlling components with additional direct-current cells in the electric circuit of the driving insert. As a result, the collecting operation can be limited to certain times of day, light conditions and/or other situations.

The invention also provides a process for collecting samples, particularly pasty masses, liquids, gases and/or other mobile objects, during a previously determinable time period in a pump cylinder characterized by filling the rearward subspace of the delivery cylinder with the consumable gas, by connecting an intake pipe in the forward cylinder space with the sample with the sample space, and by adjusting a consumption current in the gas consumption cell which, per time unit, consumes the volume of the consumption gas which is equivalent to the sample rate.

Following the sampling, an analysis of the content layered corresponding to the time-related removal and/or a mixing of the content and its analysis can then take place.

The invention preferably provides a process for collecting mobile biological objects during a previously defined time period in a pump cylinder according to the invention, in the case of which the charging of a pilot medium into the forward cylinder space takes place before the consumption current is switched on.

In a further development of the invention, a medication is preferably fed to a limited body region of a living thing (for example, an organ), and, after a predetermined time period, the medication and/or other body fluids are at least partially withdrawn again from the limited body region by means of a pump cylinder according to the invention. In this case, the invention is particularly suitable for feeding to a limited body region of a living thing (for example, an organ) an overdose of a medication by means of a syringe and to withdraw this "overdose" again from the limited body region by means of a "suction pump" according to the invention.

The pump cylinder—for example, in the form of a syringe—is closed on top preferably by the insert which, fixed in the cylinder, may, for example be sealed in and off by an O-ring and/or be screwed to the pump cylinder. A suction insert and/or driving insert, which is also sealed off by means of an O-ring, is pushed into the insert.

The driving insert contains the at least one gas consumption cell or several of these cells in a series or parallel connection. In addition, there is the Zener diode in a series connection or a diode with a corresponding threshold voltage.

The driving insert has two positions which are characterized by a bore. This bore leads into the driving insert and permits the feeding of the consumption gas into the cylinder space, in which case the plunger is driven from its uppermost position into its lowermost position. Subsequently, the driving insert is pushed into a waiting position in which the bore of the driving insert is closed. After the activation of the driving insert, the current will flow which binds the consumption gas, pulls up the plunger and causes the collection operation to take place according to the invention.

The plunger may have a bore which may be closed by a frit.

After the bore was utilized for charging the consumption gas, it is closed by means of a wetting liquid.

Additional embodiments of the invention of the invention are contained herein.

In the following, the invention will be explained in detail with reference to the drawing by means of embodiments.

DETAILED DESCRIPTION OF THE PREFERRED EMBODIMENTS

Figure 1:
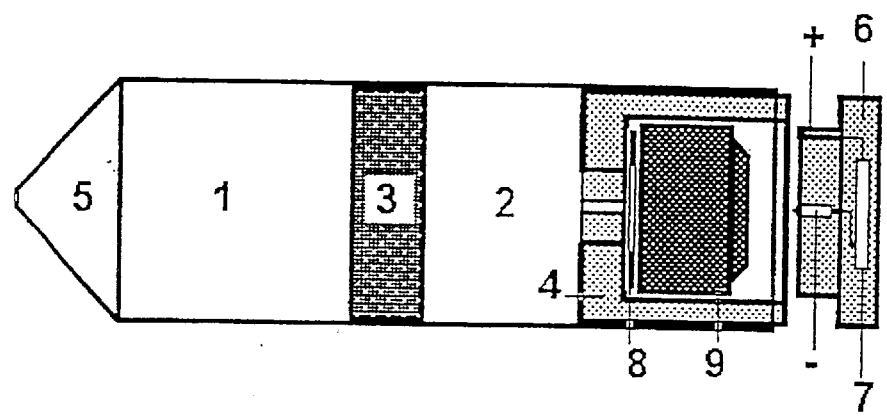
FIGS. 1 to 4 are views of various embodiments of the invention.

The device for collecting pasty masses, liquids, gases and other mobile objects for a previously definable time period—as illustrated in FIG. 1—consists of the pump cylinder in which the pump plunger 3 is guided. It divides the cylinder into a forward subspace 1 and a rearward subspace 2. The forward subspace contains the connection 5 for the fitting-on (DIN ground section), screwing-on or welding-on of a hose or a pipe socket by means of which the sample is taken in directly from the sample container.

The rearward subspace 2 of the pump cylinder contains an electrochemically consumable gas and an electrochemical gas consumption cell 9 for this gas. Reference number 4 is the sealing head of the cylinder which, together with the seal 8, contains the gas consumption cell 9. By means of an electric circuit 7 in the cover 6, a current is generated continuously or temporarily by means of the electrodes of the gas consumption cell. The current consumes an equivalent volume of the consumption gas in the rearward subspace 2. For this "destroyed" gas volume, an equally large sample volume is taken in to subspace 1.

Now the consumption gases and the pertaining consumption cells of the invention will be discussed. If the consumption gas consists of oxygen, a zinc/oxygen cell is advantageously used, as applied in a round cell form, for example, as a hearing aid cell. In the trade, these oxygen depletion cells are also often called zinc/air cells. Instead of zinc, other metals may also be used (Al, Mg, Cu); however, a voltage is endeavored which is as high as possible while the corrosion tendency in the currentless condition should be low. In this respect, zinc in the forms and alloys used in battery technology, cannot be surpassed.

Advantageously multilayer structures, as used in fuel cell technology, are used as oxygen depletion electrodes in the cells. Activated carbon in a mixture with PTFE is often used as a catalyst for the cathodic oxygen reduction. However, silver and manganese oxides are also suitable for a use as catalysts. A material with a low self-capacitance is desirable, so that the current flow alone and, if possible immediately, will be at the expense of the oxygen. The placing of the catalyst mass into a metallic network has been the state of the art for years, as has been the use of a hydrophobic cover layer made of porous PTFE facing the gas.

Instead of oxygen, hydrogen can also be used as the consumption gas. The consumption electrodes are the known hydrogen anodes of the fuel cell technology. They contain platinum, palladium or nickel as the catalysts and, in their construction, correspond to the oxygen electrodes. Hydrogen consumption cells, such as zinc/air cells, can be constructed when the zinc powder is replaced by an electrochemically active metal oxide electrode (MnO, AgO, HgO, CuO, $Cu_2O$ or CdO) and, instead of the oxygen electrode, a hydrogen electrode is used. The type of the oxide determines the voltage of the cell. In the case of all above-mentioned oxides, the consumption reaction takes place without an outside voltage source. Only in the case of the cadmium hydroxide, an additional voltage source is required because the voltage is too low, but here the consumption reaction can be reversed.

In most cases, caustic potash solution is used as the electrolyte, but other alkaline lyes are also suitable. Consumption cells can also be built by means of acidic and neutral electrolyte solutions. The electrolyte is always accommodated in a separator with a suction capacity arranged between the anode and the cathode; among other things, for preventing the admission of oxygen to the zinc electrode. This process, which can be called a self-discharge, can be completely avoided in that the consumption cell is allowed to communicate with the oxygen only when the device starts to operate in that, for example, the inlet openings of the gases to the consumption electrode are opened up only at that point.

Figure 2:
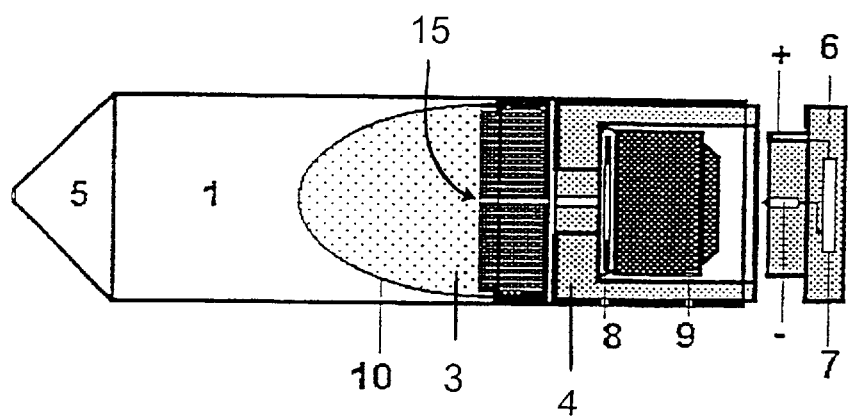

Diffusion losses of the gases may occur in the case of hydrogen as the consumption gas abut also in the case of oxygen. They can be minimized in that the respective seals are supported by bag-type foils which fill the driving cylinder space, contain the consumption cell and are penetrated only by the contact wires. This is illustrated in FIG. 2 in the manner of an example. Plungers and the elements of the gas consumption space illustrated in FIG. 1, which are the sealing head with the cell 9 and the cover 6, form the space which is filled by the foil bag 10 with the consumption gas. The foil also encloses consumption cell 9, for which it forms the sealing. The two housing parts of the cell—these are the cup and the cover—are accessible from the outside and can be connected with the contacts of the electric circuit so that it is possible to move through all current-time profiles.

In the case of the particularly suitable zinc/oxygen variant, the voltage will be above 1 V as long as oxygen is still present. Then it will suddenly break down. So that subsequently no hydrogen development will take place, by using a rectifier diode or Zener diode poled in the flow direction, it is provided that the cell voltage does not drop below 0.4 V. Also any other electrical switching which keeps the voltage of the cell out of the voltage window of the hydrogen development is suitable for this purpose. It is particularly skillful to couple the consumption of the consumption gas with the extinguishing of an operational display signal. This may consist, for example, of a light-emitting diode, of an LCD field or of an acoustic buzzer.

In the simplest case, the construction of the device according to the invention consists of the delivery cylinder, of the plunger which divides the cylinder into the forward cylinder space for receiving the samples and into the rearward cylinder space for the consumption gas, and the consumption cell. The forward cylinder space changes into an intake pipe with an optional return valve. The consumption gas and the consumption cell may be enclosed by a plastic or rubber membrane. According to the invention filed under File Number 199 09 014.9, the plunger may contain a bore, or bypass bore 15 and a rubber-elastic membrane bag which is fastened by means of the upper edge in a firm and gastight manner to the plunger, the shape of the unfolded membrane bag being adapted to the interior of the delivery cylinder.

The bypass bore 15 contains a valve which is closed during the movement of the plunger from the spout to the head for taking in the flowable medium. When the delivery gas is charged, the valve opens up and releases the path for the consumption gas into the rubber-elastic membrane bag. The latter fills the forward cylinder space completely.

During a current reversal, the gas electrode used in the consumption cell reverses the flow direction of the gas; it therefore changes from the gas consumption to the generating of gas. When an accumulator electrode is used as the counterelectrode, as the result of a current reversal, the driving cylinder can be filled with consumption gas and the consumption cell can be regenerated. The regenerated condition can be recognized by the position of the plungers and can be used for switching off the regenerating current. Cell combinations of this type are $H_2/CdO$ and $H_2/NiOOH$ as well as $O_2/Cd(OH)_2$ and $O_2/Ni(OH)_2$, to mention two examples respectively for hydrogen and oxygen consumption cells which can be regenerated. Particularly in the case of the often used systems, a system which can be regenerated may be found to be economical.

A gas-operated delivery device for flowable media with a gas consumption system which "destroys" gas volume in a predefined time-related quantity in gas consumption cells which have a cylindrical space with an intake opening and a plunger 3 which divides the cylinder into a forward subspace 1 for receiving the medium to be delivered and into a second subspace 2 which contains the gas consumption system and the consumption gas, may also be designed such that the sealing head 4 and the plunger 3 form a unit which is movable in the cylinder and has a rubber-elastic membrane bag which is fastened in a gastight manner to the plunger 3. The unit, consisting of the sealing head and the plunger contains the gas consumption system and the electric circuit and, in the upper part, has a device for fastening a push tube for the manual movement of the unit in the delivery cylinder.

The application sequence takes place in four phases: In the first phase, the unit consisting of the plunger and the folded delivery bag is connected in a gastight manner such with a push tube 13, which can be screwed in or inserted, that no air can penetrate into the interior formed of the plunger and the bag 10. By way of the push tube 13, the bag 10 is connected with the source of the consumption gas and is inflated by pumping until it completely fills the cylinder space. Subsequently, the sample medium is contacted by way of the optional hose and spout. Then the push tube 13 is sealed off and possibly unscrewed and the gas consumption cells 9 are activated by means of the electric closing circuit 7.

Figure 3:
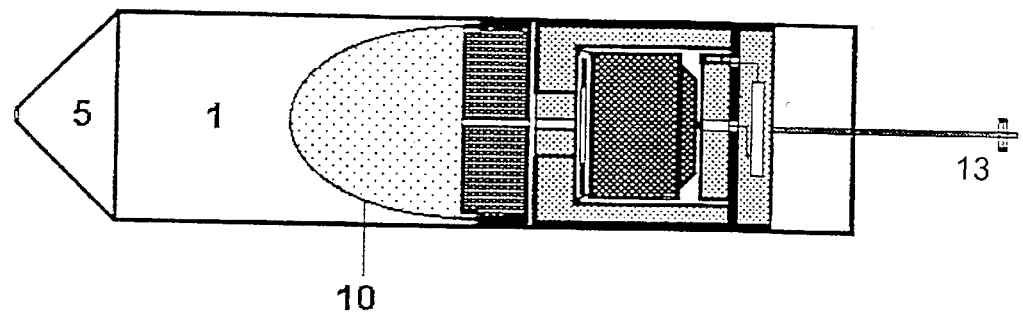

For the effect of the membrane bag, it is important that it can unfold without any problem and can be folded again. This can be achieved particularly successfully when it has the shape of a rotational body with a zigzag line or sinusoid as the generating rotation curve. Thus, as illustrated in FIG. 3, the bag 10 can be pushed onto a mandrel-type attachment on the frame of the plunger, from which it is lifted when the consumption gas is introduced and is unfolded. In this manner, it is possible to minimize the influence of the clearance volume. The tip of the unfolded delivery bag is expediently shaped as a hemisphere. In any case, because of its rubber-elastic characteristics, it is adapted to the delivery cylinder at the end of the charging of the gas.

As mentioned above, the forward subspace 1 contains the connection 5 for the fitting-on (DIN ground section), screwing-on or welding-on of a hose or of a pipe socket by means of which the sample can be taken in directly from the sample container. In this intake pipe, an analyzing chamber may be situated in which the sample is analyzed "online", for which electric, magnetic, optical, spectroscopic and other measuring methods are suitable. The rearward subspace 2 of the pump cylinder is bounded in the forward direction by the plunger 3 and in the rearward direction by the sealing head 4 of the cylinder. By means of the electric current, the gas is consumed and stationarily for this "destroyed" gas volume, an equally large sample volume is taken in. The friction (static friction and sliding friction) of the plunger 3 during the movement in the cylinder, which requires a pressure difference between spaces 1 and 2, plays an important role in these events. The lower the intake rate and therefore the lower the consumption current of the gas, the longer the time to the start of the plunger movement, which is called idle time in this case. In order to shorten or suppress this idle time, the following methods can generally be used. A starting current Is and a working current Ia are used which can be switched on by two different electrical circuit elements (resistors). Is will be switched on until the plunger starts to move. Then this current is switched off and—possibly after an arbitrary rest period—the working current Ia is switched on. When a potentiometer is used as a controllable resistor for the adjustment of the consumption cell current, a starting current adjustment is marked from which a change takes place manually or by means of a time switch into the variable working current adjustment. In the case of a manual switching, the point in time of the termination of the starting operation can be recognized by the beginning plunger movement. However, the switching-off of the starting current can also be caused by means of a pressure switch which is analogously operated by the pressure difference between the spaces 1 and 2. In the case of a time switching, the gas consumption ($\Delta n$) by the starting current (Is) flowing for the time ($\Delta t$) must be so large that the resulting pressure reduction ($\Delta p$) in the consumption gas space (2) is equal to the friction force (Kr) of the plunger in the cylinder. When Q is the cylinder cross-section, Vo is the starting volume of the space (2), po is the starting pressure, $\Delta pr=Kr/Q$ is the pressure difference ($\Delta pr$) for overcoming the friction. The pressure difference caused by the starting current Is in the time $\Delta t$ is $\Delta p=(RT/zF)(Is/Vo)\Delta t$. By equating the two expressions for $\Delta p$ and $\Delta pr$ and the conversion, the required time ($\Delta t$) is found to the beginning movement of the plunger at $\Delta t=Kr*(Vo/Q)/(RT/zF)/Is$. Example: Kr=3 N, Q=25.5 $cm^2$, (RT/zF)=0.007 V, Is=1.25 V/100$\Omega$=0.0125 A result in the starting time $\Delta T$=807 s=13.4 min=0.22 h. Thus, as early as after 13 minutes, a switching can take place to the working resistance, for example, 1,000$\Omega$. However, solely by means of this resistance, the movement of the plunger would start as late as after two hours.

Figure 4:
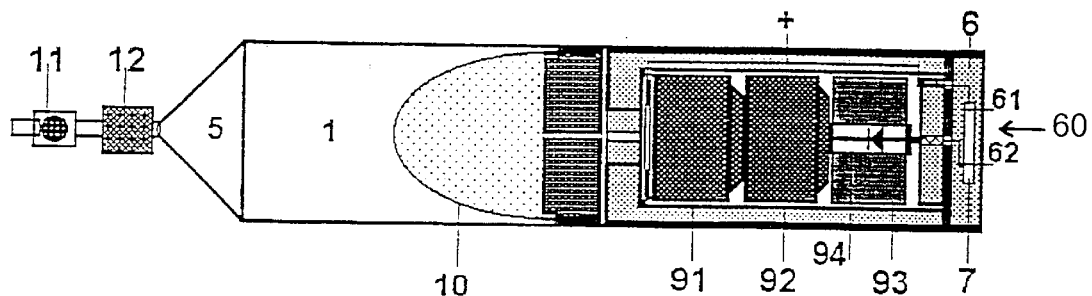

As an example, FIG. 4 is an overall representation of the invention. By way of the return valve 11 (ball valve), the fluid medium in the online analyzer 12, at reference number 5, is taken into the sample space 1. The consumption gas is situated in the membrane bag 10 and in the remaining cylinder space. The latter contains in the "driving head", which can be inserted as a component—see FIG. 5—into the cylinder space, the consumption cells 91 and 92 in a series connection with the diode element 93. The latter advantageously has the same dimensions as the cells. This diode element contains the diode 94 which, by means of its threshold voltage, determines the minimum voltage of the battery set at which the consumption current can still flow and prevents the current reversal after the consumption of this gas and therefore has the function of a self-reacting switch. The current is adjusted by means of the potentiometer resistance 60 which is determined here by the two positions 61 (starting current) and 62 (working current). In addition, the potentiometer may contain an on/off switch.

Figure 5:
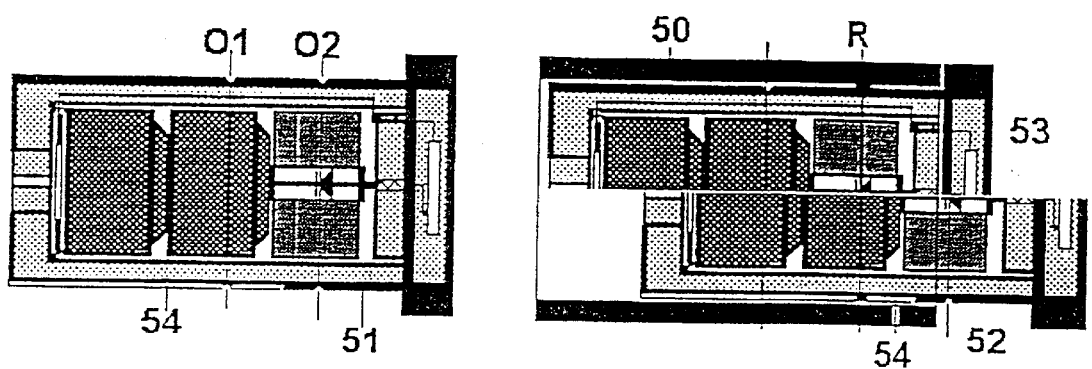
FIG. 5 is a view of a preferred further development of the upper area of the cylinder and of the driving element which can be inserted.

FIG. 5 illustrates a preferred embodiment of the upper region of the cylinder 50 and of the plug-type driving element 51. In the left figure, O1 and O2 are two ring grooves in the exterior of the cylindrical driving head. The sealing ring placed in an interior groove R of the cylinder 50 corresponds to the two ring grooves. This arrangement permits two stable plug-in positions 52 and 53 of the driving head 51 in the cylinder 50, which are demonstrated in the lower and the upper half, respectively. In the drawn-out position 52 in the lower figure portion, the gas duct 54 connects the upper region of the cylinder with the subspace 2 between the plunger 3 and the driving head or with the interior of the gas membrane 10. It therefore permits the introduction of the consumption gas into the apparatus through a fitted-on gas hose. In this case, the plunger 3 is moved in FIG. 1 from the upper position into the lower position or the membrane bag 10 is inflated in FIG. 2. After this has taken place, the driving head is pressed into the end position 53 which is illustrated in the upper part of the cylinder. By means of the adaptation of the upper cylinder region 50, a plurality of syringes of different sizes can be equipped with one and the same driving head.

Figure 6:
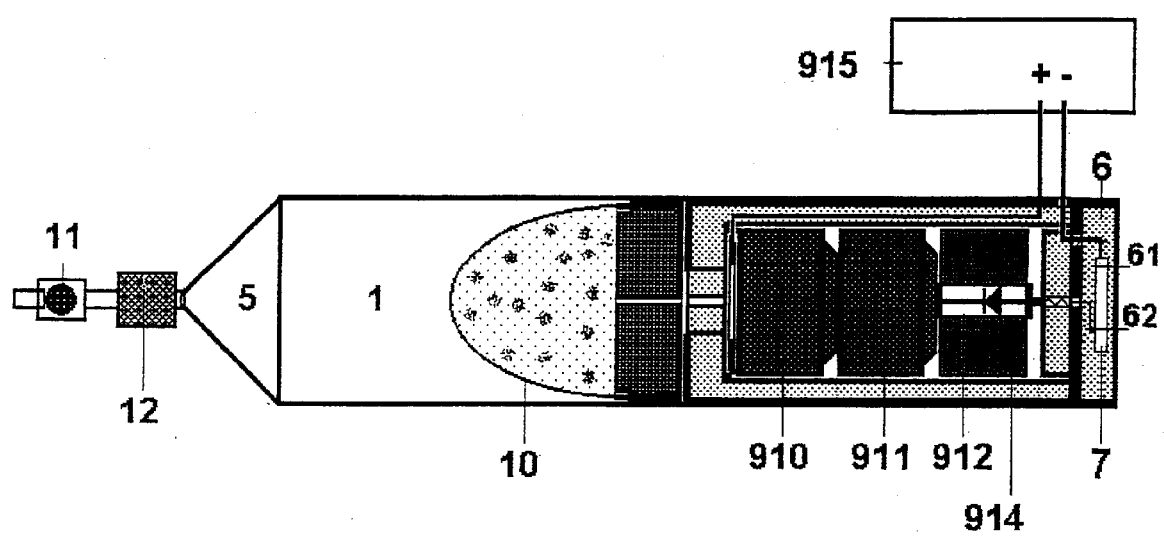
FIG. 6 is a view of another embodiment of the present invention that includes a regulation unit.

FIG. 6 is another embodiment of the present invention that shows bag 10, which contains consumption gas. Cells 910, 911 represent two consumption cells in series connection with diode 912 in element 914. Elements 910, 911, 912, together form a gas consumption unit which determines the voltage range of the gas consumption process or operation. The diode 912 can be of the rectifier-type (for example, Si-diode or Ge-diode) or a Zener diode or an illumination or laser diode.

As shown in FIG. 6, regulation unit 915 is for switching on and regulating current. The unit 915 may contain an additional battery, an optical or an acoustic signal device or generator or other similar equipment which generates a signal when the current flow takes place in a voltage range which permits a gas consumption to take place.

What is claimed is:

1. A pump cylinder comprising:
   a) a pump plunger guided in and dividing the cylinder into a forward and a rearward subspace;
   b) the forward subspace has a connection for taking in a fluid medium to be delivered;
   c) the rearward subspace contains at least one electrochemical cell for a consumption gas;
   d) an electric circuit being constantly or temporarily connected with electrodes of the cell;
   e) the rearward part of the pump cylinder being filled with an electrochemical consumption gas and being closed;
   f) the cell being a gas consumption cell for the consumption gas; and
   g) the electric circuit having a working resistor and is designed for causing a gas consumption current so that the pump cylinder forms a device for collecting pasty masses, liquids, gases and mobile objects for a predetermined time period.

2. A pump cylinder according to claim 1, wherein the consumption gas and the consumption cell are separated from the forward subspace by a deformable plastic foil bag.

3. A pump cylinder according to claim 1, wherein the consumption gas is oxygen and the consumption cell, in addition to a gas diffusion electrode for oxygen, contains an accumulator electrode as a counterelectrode.

4. A pump cylinder according to claim 1, including a valve in the connection for taking in the fluid medium to be delivered which valve opens up in the suction direction when there is a vacuum and shuts off in the outflow direction when there is excess pressure.

5. A pump cylinder according to claim 1, wherein the electric circuit permits a current flow in the consumption cell only in a voltage range in which the gas consumption takes place and shuts off the current flow in the remaining voltage ranges.

6. A pump cylinder according to claim 5, wherein the electric circuit contains an optical or acoustic signal generator which generates a signal when the current flow takes place in the voltage range which permits the gas consumption to take place.

7. A pump cylinder according to claim 1, wherein the working resistor is an adjustable working resistor, and including a starting resistor which short-circuits the consumption cell until the movement of the plunger starts.

8. A pump cylinder according to claim 7, wherein, for switching off a starting current, a manual switch or a pressure switch is provided which responds to the pressure difference at both sides of the plunger or to the movement of the plunger from a starting position of the plunger in the cylinder.

9. A pump cylinder according to claim 1, including time switches, photoresistors and/or photocells, as controlling components for the consumption cell with additional direct current cells, limit a collecting operation to certain times of day, light conditions and/or other situations.

10. A pump cylinder according to claim 1, wherein the pump cylinder is closed by an insert which is fixed and/or sealed off in the pump cylinder, and into which a suction and/or driving insert is pushed in a sealed-off condition which contains the at least one gas consumption cell and/or a Zener diode or a diode with a corresponding threshold voltage.

11. A pump cylinder according to claim 1, wherein the plunger has a closable bore with a closure.

12. A pump cylinder according to claim 1, wherein the consumption gas has an inert gas admixture.

13. A pump cylinder according to claim 1, including an analyzing device preferably integrated in an intake pipe.

14. A process for collecting samples, preferably pasty masses, liquids, gases and/or other mobile objects, during a predetermined time period in the pump cylinder according to claim 1, the process comprising:
   a) filling the rearward subspace of the cylinder with the consumption gas,
   b) connecting an intake pipe in the forward subspace of the cylinder with a sample space, and
   c) adjusting a consumption current in the gas consumption cell which per time unit consumes the volume of the consumption gas equivalent to a sampling rate.

15. A process according to claim 14, including analyzing a content of a collected sample layered corresponding, to the time-related removal or mixing of the content.

16. A process according to claim 14 for collecting mobile biological objects including charging a pilot medium into the forward subspace of the cylinder before the consumption current is switched on.

17. A process according to claim 14 including supplying a medication to a limited body region of a living thing, and after a predetermined time period and/or at an offset point of the body, a body fluid and/or at least partially the medication is withdrawn again from the limited body area by the pump cylinder.

18. A process according to claim 17, wherein the limited body region is an organ.

* * * * *